United States Patent [19]

Ranganathan

[11] 3,948,883

[45] Apr. 6, 1976

[54] SYNTHESIS OF PURINE NUCLEOSIDES

[75] Inventor: Ramachandran S. Ranganathan, Rowland Heights, Calif.

[73] Assignee: The Salk Institute for Biological Studies, San Diego, Calif.

[22] Filed: Nov. 11, 1974

[21] Appl. No.: 522,492

[52] U.S. Cl. .......................... 260/211.5 R; 424/180

[51] Int. Cl.$^2$ .......................................... C07H 19/16

[58] Field of Search .............................. 260/211.5 R

[56] References Cited

UNITED STATES PATENTS 3,658,788 4/1972 Orgel et al. .................. 260/211.5 R

*Primary Examiner*—Johnnie R. Brown
*Attorney, Agent, or Firm*—Fitch, Even, Tabin & Luedeka

[57] ABSTRACT

A desired purine-containing nucleoside is synthesized by condensing a nitropyrimidine with a thionoxazolidine that is an adduct of a sugar unit and an oxazolidine ring unit having two adjacent carbon atoms in common. Prior to condensing the thionoxazolidine is converted to the bromo-mercuric derivative to promote the reaction at the nitrogen site. The N-alkylated condensation product is reduced to produce an amino-pyrimidine nucleoside which is then heated under conditions to cyclize it to a mercapto-purine nucleoside. The cyclized product is finally desulfurized to produce the desired purine-containing nucleoside. The compounds are useful as anti-viral agents.

15 Claims, No Drawings

SYNTHESIS OF PURINE NUCLEOSIDES

The invention described herein was made in the course of work under a grant or award from the Department of Health, Education, and Welfare.

BACKGROUND OF THE INVENTION

This invention relates generally to nucleosides and more particularly to the synthesis of purine-containing nucleosides. For example, it provides an efficient route for the synthesis of 9-β-D-arabinofuranosyl adenine (hereinafter referred to as ara-A), which is an important, naturally-occurring anti-viral agent that has shown significant activity against herpes simplex and vacinia viruses in tests performed on cell cultures and on experimental animals.

One method heretofore used for the synthesis of ara-A has been the modification of preformed nucleosides, as reported in the article authored by E. J. Reist et al. appearing in the *Journal of Organic Chemistry*, Volume 27, Page 3274 (1962), and also in the article by M. Ikehara and Y. Ogiso, appearaing in Tetrahedron, Volume 28, Page 3695 (1972). Ara-A has also been synthesized from arabinose and its derivatives as reported in the article by C. P. J. Glaudemans and H. G. Fletcher, Jr., appearing in the Journal of Organic Chemistry, Volume 29, Page 3286 (1964) and in the article by G. Lunzmann and G. Schramm, appearing in *Biochemica and Biophysica Acta*, Volume 169, Page 263 (1968). However, these known syntheses have not been entirely satisfactory in that the yields were often low. New syntheses for preparing purine-containing nucleosides which can be efficiently and economically carried out using readily available starting materials are desired.

SUMMARY OF THE INVENTION

It has been found that purine-containing nucleosides, such as ara-A, can be prepared by the N-alkylation of a thionoxazolidine using a 6-halogeno-5-nitropyrimidine. The thionoxazolidine is first prepared by reaction with a mercuric compound, such as mercuric bromide, to provide the bromo-mercuric derivative thereof which avoids the creation of unwanted S-alkylated products. Following the condensation reaction, the nitropyrimidine nucleoside is reduced to provide the aminopyrimidine nucleoside and thereafter is cyclized to produce the 8-mercapto-purine nucleoside. Finally, desulfurization takes place to give the desired purine-containing nucleoside.

The starting materials are readily available; for example, the thiocyanic acid adducts of a variety of sugars may be used. The N-alkylated condensation products are versatile intermediates useful in the preparation of modified purine nucleosides. The synthesis process is particularly valuable because it provides excellent yields of the precise structure desired with substantially no creation of stereoisomers. Moreover, the nature of the synthesis is such that it is not necessary to protect the side hydroxyl or other groups on the sugar unit, as they are not affected by the steps of the reaction. Thus, the synthesis lends itself to the employment of naturally occurring sugars or modified sugars, as well as the use of modified pyrimidines. The N-alkylated products are highly useful as chemical intermediates for the synthesis of naturally-occurring compounds as well as non-naturally occurring nucleosides which often shown considerable biological activity. As such, the compounds are considered extremely valuable both to fundamental research and to the pharmaceutical industry. Such nucleosides can be important in the further synthesis of oligonucleotides and nucleic acids, in the studies of metabolism and genetic mechanisms and in the synthesis of vitamins and other biological compounds.

DESCRIPTION OF THE PREFERRED EMBODIMENTS

Very generally, the invention provides syntheses which utilize readily available starting materials such as the thiocyanic acid adducts of naturally occurring or modified sugars. The sugars may be monosaccharides, disaccharides or polysaccharides, and they may be either aldoses or ketoses. The preferred monosaccharides have from 2 to 12 carbon atoms and include glycoaldehyde, glyceraldehyde, erythrose, ribose, arabinose, glucose, fructose, sorbose, mannose, galatose, dihydroxyacetone, erythrulose, xylulose and ribulose. The disaccharides include lactose and maltose, and the polysaccharides include maltotriose and manninotrose. Both the D- and L-stereoisomers of the aforementioned sugars may be used.

Modified or substituted sugars may be used, wherein one or more hydrogen atoms in the hydroxyl groups other than those at which the reaction with the thiocyanic acid will take place may be replaced by various radicals, such as phosphate, acetyl, benzoyl, tetrahydropyranyl, benzyl, trityl (triphenylmethyl) and trimethylsilyl. Examples of substituted sugars include ribose-3-phosphate; ribose-5-phosphate; arabinose-3-phosphate; arabinose-5-phosphate; arabinose-3-5-diphosphate, glyceraldehyde-3-phosphate; 3,5-di-O-acetyl-D-ribose; 3,5-di-O-benzoyl-D-arabinose, 3,5-ditetra-hydropyranylarabinose, 3,5-dibenzylarabinose, 5-tritylarabinose and 5-tritylribose.

The reaction with the thiocyanic acid to form the sugar adduct takes place at the No. 1 carbon atom and with the hydroxyl group connected to the No. 2 carbon atom. The adduct can be prepared in good yield using the general procedure as set forth in the article by W. H. Bromund and R. M. Herbst appearing in *Journal of Organic Chemistry*, volume 10, Page 267 (1945). For the preparation of ara-A or a substituted form thereof, arabinofurano-thionoxazolidine having the following formula is used:

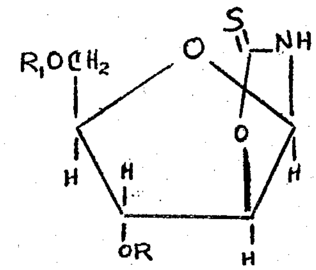

wherein R is hydrogen, phosphate, acetyl, benzoyl, tetrahydropyranyl or benzyl and wherein $R_1$ is hydrogen, phosphate, acetyl, benzoyl, tetrohydropyranyl, benzyl or trityl.

It is important that the thionoxazolidine adduct be treated so that the contemplated alkylation occurs at the nitrogen site and not at the sulfur site. It has been found that the sulfur site can be effectively removed from participation in the subsequent alkylation reaction by forming a mercuric derivative thereof. A suitable mercuric compound, such as mercuric chloride, mercuric bromide, mercuric acetate or the like is used, with mercuric bromide being preferred. The treatment is carried out under nonaqueous conditions by dissolving the adduct in a suitable inorganic solvent, such as N,N-dimethylformamide (DMF), and by pretreating with sodium hydride to form the sodium salt at the site. Thereafter, addition of the mercuric compound presumably causes a mercuric derivative to be formed at the sulfur atom, which thereafter prevents any substantial alkylation from taking place at this site. Mercuric bromide adds stoichiometrically to the thionoxazolidine adduct and is accordingly employed in about 1 to 1 mole ratio.

With the thionoxazolidine adduct prepared as indicated above, the alkylation reaction with a suitably active pyrimidine is carried out. In order to provide the desired final product, ara-A, a pyrimidine is chosen having a nitro group at the No. 5 carbon atom site and a halogen at the No. 6 carbon atom site. This nitropyrimidine shows excellent activity for alkylation in a nonaqueous environment whereas the corresponding 5-amino pyrimidine has been found to be unreactive. Acid catalysis is an aqueous medium might promote this reaction, but these conditions would be undesirable because of potential hydrolysis of other groups on the adduct.

The pyrimidine may be substituted at other locations also, and the following formula is considered to represent suitable halogenated pyrimidines that may be employed:

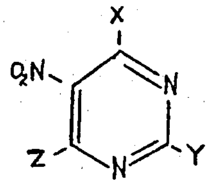

The group Z represents the halogen and is preferably chlorine, inasmuch as it is most readily available and appears to give the most complete reaction; however, it may also be bromine or iodine. The group X on the No. 4 carbon atom may be NHR′, $NR'_2$, F, Cl, OR′, or SR′ (wherein R′ is hydrogen or lower alkyl), with amino being preferred. The group Y on the No. 2 carbon atom may be H, F, Cl, NHR′, $NR'_2$, OR′ or SR′ (wherein R′ is hydrogen or lower alkyl). Lower alkyl is used to mean up to about five carbon atoms in the chain.

The presence of the nitro group on the No. 5 carbon atom creates a tendency for the condensation reaction to take place at the No. 6 carbon atom of the pyrimidine molecule, and the blockage of the sulfur site on the adduct by the mercuric ion assures that the reaction proceeds substantially only at the amino site thereon. The reaction proceeds stoichiometrically, and the pyrimidine is provided in about a 1 to 1 mole ratio with the adduct. The reaction proceeds slowly and may be carried out in the same non-aqueous solution employed for the addition of the mercuric compound to the adduct. At the completion of the condensation reaction, the mercuric ion is removed from the nucleoside as insoluble mercuric iodide by treatment with a soluble iodide, such as potassium iodide.

The resultant nitro-thione nucleoside is somewhat unstable to hydrolytic conditions, and it has accordingly been found advantageous to reduce the nitro group to the amino group. Suitable hydrogenation catalysts may be employed, and two which have been found to be effective are paladium deposited upon a carbon substrate and an aluminum amalgam catalyst. About 10 percent by weight paladium deposited on the extremely large surface area provided by a porous carbon substrate has proved to be an effective catalyst. The aluminum amalgam catalyst can be prepared from aluminum foil and mercuric chloride using known methods.

Following the reduction of the nitro group, the nucleoside is appropriately purified and then dissolved in water wherein suitable heating is carried out to sever the oxazolidine ring and cause cyclization to the purine moiety. Heating for several hours at 70°C. or above is sufficient to complete the cyclization. The reaction proceeds to completion in the aqueous solution producing the 8-mercaptopurine nucleoside.

Desulfurization may be carried out by a conventional method to achieve the desired resultant product. For example, desulfurization may be effected by treatment with hydrogen peroxide in aqueous methanol in the presence of hydrochloric acid. Heating to about 90°C. with Raney nickel in aqueous ammonia provides even more efficient desulfurization and is preferred.

The overall process provides an excellent synthesis of purine-containing nucleosides from thionoxazolidine-sugar adducts in yields of about 40 percent. These very high yields for a synthesis of this type are available because of the lack of formation of undesirable stereoisomers and because of the lack of occurrence of side reactions to any significant extent. Moreover, the overall reaction conditions are such as to be considered to have good efficiency and not to be overly time-consuming nor requiring of high precision in control.

The following Example is illustrative of the preparation of ara-A but should not be considered to constitute limitations upon the scope of the invention which is defined solely by the claims.

EXAMPLE

The synthesis of ara-A is performed beginning with seven grams (36.6 millimoles) of arabinofurano-[1′,2′-4,5]-2-oxazolidine-2-thione, which is prepared by the treatment of arabinose with thiocyanic acid to form the adduct. A slight excess of sodium hydride (1.77 gram; 37.1 m.mole) is first washed with dry benzene and is then suspended in 50 milliliters of dry DMF in a one-liter round-bottom flask. After cooling the suspension in an ice bath, the adduct is added dropwise with stirring as a solution in 100 milliliters of DMF. The ice bath is removed, and the mixture is allowed to come to room temperature. When the evolution of hydrogen ceases, 13.2 grams of mercuric bromide (36.6 m.mole) is added to the solution to form the bromo-mercuric derivative at the sulfur site of the adduct.

6.4 grams of 4-amino-6-chloro-5-nitropyrimidine (36.6 m.mole), dissolved in 100 milliliters of DMF, is slowly added to the solution. The reaction mixture is slowly stirred and allowed to remain at room temperature for three days for the condensation reaction to proceed to completion. Thereafter, the mixture is filtered and then freed of solvent under vacuum at about 40°C. Two hundred milliliters of ethylacetate is added to the residue, followed by 100 milliliters of an aqueous solution of 30 percent potassium iodide.

After vigorous shaking for a few minutes, the ethylacetate layer is separated and then washed again with two 25-milliliter portions of the potassium iodide solution, followed by two 25-milliliter portions of a dilute aqueous sodium chloride solution and finally with a 25-milliliter portion of a saturated aqueous sodium chloride solution. The washings are carefully re-extracted with ethylacetate, and the organic layers are all combined, dried over magnesium sulfate and the solvent removed. A foamy, yellow residue results, and about 200 milliliters of dioxane is added thereto to create a suspension which is stirred. The amino-nitropyrimidinyl-thiono-oxazolidine dissolves in the dioxane, leaving only a finely divided insoluble precipitate which is filtered off.

The dioxane solution is added with mechanical stirring to a suspension of aluminum amalgam in 200 milliliters of methanol, prepared from 5 grams of aluminum foil following the procedure described in *Reagents for Organic Synthesis*, Volume 1, page 20 (1967) by L. F. Fieser and M. Rieser. After 1 hour, the mixture is filtered through Celite, and the precipitate is repeatedly extracted with boiling methanol (5 × 100 ml). The extracts are combined with the filtrate, and the solvents are removed in vacuo.

The residue is dissolved in 150 milliliters of water and then heated under a nitrogen atmosphere to a temperature of 80°C. to 85°C. for about four hours to effect the cyclization and create the purine moiety. The solution turns deep brown and is decolorized using about 500 milligrams of Norit.

The pH of the resulting solution is adjusted to about 7.5 by the addition of concentrated $NH_4OH$, and 6 grams of Raney nickel are added. Desulfurization is then carried out by heating the aqueous solution to a temperature of about 90°C. to 95°C. for about 2-½ hours. The mixture is then filtered while hot to remove the Raney nickel catalyst, and the filtrate is chilled in ice. Suction filtration collects the ara-A compound in the form of white needles in the amount of 3.66 grams (equal to a yield of 37 percent), which compound has the following formula:

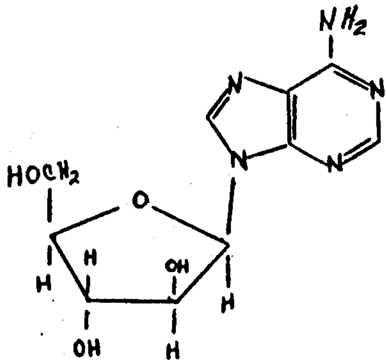

The compound is tested and found to be pure, having a melting point of 254°–255°C. By washing the nickel catalyst with warm water and combining it with the mother liquor, followed by crystallization from methanol, another 0.2 gram of ara-A is obtained, bringing the total yield to 39.4 percent.

Modifications to the foregoing described syntheses which would be obvious to one having the ordinary skill in this art are considered as coming within the scope of the invention which is defined by the claims appended hereto.

Various of the features of the invention are set forth in the following claims.

What is claimed is:

1. A process for synthesizing a desired purine-containing nucleoside comprising a. condensing a thionoxazolidine with nitropyrimidine having the following formula:

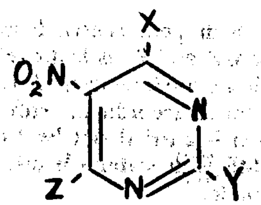

wherein X is NHR', $NR'_2$, fluoro, chloro, OR', or SR', wherein R' is hydrogen or lower alkyl, Y is H, $CH_3$, fluoro, chloro, NHR', $NR'_2$, OR' or SR' wherein R' is hydrogen or lower alkyl, Z is Cl, Br or I, Said thionoxazolidine comprising an adduct of a sugar unit and an oxazolidine ring unit having the carbon atoms in the 1,2 positions on the sugar unit in common; said sugar unit being selected from the group consisting of monosaccharides, disaccharides and polysaccharides;

b. reducing the N-alkylated condensation product to produce an amino-pyrimidine nucleoside;

c. heating said amino-pyrimidine nucleoside under conditions to cyclize same to a mercapto-purine nucleoside; and d. desulfurizing said cyclized product to produce the desired purine-containing nucleoside.

2. A process in accordance with claim 1 wherein said thionoxazoldine is treated with mercuric bromide to convert it to the bromomercuric derivative thereof prior to said condensation reaction.

3. A process in accordance with claim 1 wherein said sugar unit is selected from the group consisting of glycolaldehyde, glyceraldehyde, erythrose, ribose, arabinose, glucose, fructose, sorbose, mannose, galactose, dihydroxyacetone, erythrulose, xylulose, ribulose, lactose, maltose, maltotriose and manniotriose.

4. A process in accordance with claim 1 wherein said sugar unit is arabinose.

5. A process in accordance with claim 4 wherein said condensation reaction is carried out at a mole ratio of about one mole of said nitropyrimidine to each mole of said thionoxazolidine.

6. A process in accordance with claim 5 wherein X is $NH_2$, Y is H and Z is Cl.

7. A process in accordance with claim 1 wherein said cyclization is carried out under an inert atmosphere by heating to a temperature of at least about 70°.

8. A process in accordance with claim 1 wherein said desulfurization is carried out by heating in the presence of Raney nickel.

9. A process in accordance with claim 1 wherein said thionoxazolidine has the formula:

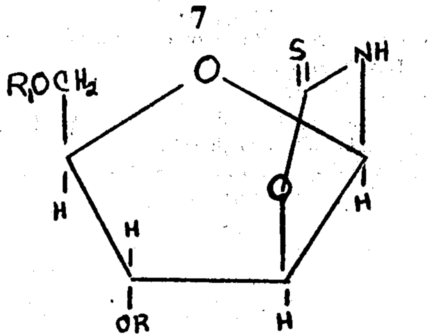

wherein R is hydrogen, acetyl, benzoyl, tetrahydropyranyl, or benzyl and $R_1$ is hydrogen or acetyl, benzoyl, tetrahydropyranyl, benzyl, or trityl.

10. A process in accordance with claim 2 wherein said conversion is carried out by treating a solution thereof in DMF with sodium hydride and then with mercuric bromide.

11. A process in accordance with claim 10 wherein said condensation reaction is carried out by adding said nitropyrimidine to said solution of said mercuric bromide derivative.

12. A process for N-alkylating a thionoxazolidine compound, which comprises treating said compound in a nonaqueous solution with a mercuric compound to form the mercuric derivative thereof by addition to the sulfur site, and thereafter reacting said mercuric derivative with a pyrimidine halide.

13. The process of claim 12 wherein treatment with sodium hydride is carried out prior to addition of said mercuric compound.

14. The process in accordance with claim 13 wherein said mercuric compound is selected from the group consisting of mercuric bromide, mercuric chloride and mercuric acetate.

15. The process in accordance with claim 14 wherein said reaction is carried out with a compound having the following formula:

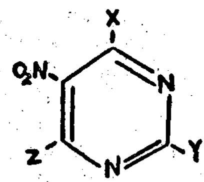

wherein X is NHR', $NR'_2$, F, Cl, OR' or SR', wherein Y is H, $CH_3$, F, Cl, NHR', $NR'_2$, OR' or SR', and wherein Z is Cl, Br or I, R' being hydrogen or lower alkyl.

* * * * *

UNITED STATES PATENT AND TRADEMARK OFFICE

CERTIFICATE OF CORRECTION

PATENT NO. : 3,948,883

DATED : April 6, 1976

INVENTOR(S) : R. S. Ranganathan

It is certified that error appears in the above-identified patent and that said Letters Patent are hereby corrected as shown below:

Column 1, line 68 - "shown" should be --show--.

Column 6, line 63 "70°" should be --70°C.--.

Signed and Sealed this

Seventeenth Day of August 1976

[SEAL]

*Attest:*

RUTH C. MASON
*Attesting Officer*

C. MARSHALL DANN
*Commissioner of Patents and Trademarks*